| United States Patent [19] | [11] Patent Number: 4,950,769 |
|---|---|
| McCandless et al. | [45] Date of Patent: Aug. 21, 1990 |

[54] PROCESS FOR THE MANUFACTURE OF MALEIC ANHYDRIDE UTILIZING PEROXIDES TO IMPROVE CATALYTIC ACTIVITY

[75] Inventors: Henry A. McCandless, Joliet; John L. Cearley; Hassan Taheri, both of Naperville, all of Ill.

[73] Assignee: Amoco Corporation, Chicago, Ill.

[21] Appl. No.: 397,389

[22] Filed: Aug. 23, 1989

[51] Int. Cl.$^5$ ............................................. C07D 307/60
[52] U.S. Cl. .................................... 549/257; 549/259; 549/260
[58] Field of Search ...................... 549/257, 259, 260

[56] References Cited

U.S. PATENT DOCUMENTS 2,954,385  9/1960  Burney et al. ...................... 549/257

Primary Examiner—John M. Ford
Assistant Examiner—Bernard I. Dentz
Attorney, Agent, or Firm—Gunar J. Blumberg; William H. Magidson; Ralph C. Medhurst

[57] ABSTRACT

A process for the manufacture of maleic anhydride using phosphorus-vanadium catalyst and peroxide modifiers.

31 Claims, No Drawings

PROCESS FOR THE MANUFACTURE OF MALEIC ANHYDRIDE UTILIZING PEROXIDES TO IMPROVE CATALYTIC ACTIVITY

FIELD OF THE INVENTION

The field of this invention relates to the use of peroxides to improve the catalytic activity of phosphorus-vanadium catalysts used for the oxidation of benzene or $C_4$ hydrocarbon feedstocks to maleic anhydride. The peroxides are added in an amount of from about 1 to about 10,000 parts per million of the total reactor feed gas stream.

BACKGROUND

Maleic anhydride is of significant commercial interest throughout the world and is extensively used in the production of alkyd resins. It is also a versatile intermediate for chemical synthesis. Consequently, large quantities of maleic anhydride are produced each year to satisfy these needs.

In general, catalysts utilized for the oxidation of benzene and $C_4$ hydrocarbons, such as butene, butane, and butadiene, to maleic anhydride are based upon vanadium and phosphorus. Various metal activators have been used to enhance the phosphorus-vanadium catalyst. The difficulty with the phosphorus-vanadium metal-promoted catalysts is that they tend to deactivate quite quickly. In this connection, U.S. Pat. Nos. 4,020,174, 4,094,816, and 4,089,807 teach that carbon tetrachloride can be used to reactivate the vanadium-phosphorus cometal-promoted catalyst. In U.S. Pat. No. 3,296,282 and U.S. Pat. No. 3,474,041, there is described a method for the regeneration of vanadium-phosphorus oxidation catalysts used in the oxidation of olefins to make maleic anhydride. These references disclose the process of treating the catalyst with a phosphine, phosphite or phosphonate by periodically or continuously passing the phosphorus compound to the reactor, with or without interrupting the olefin feed flow. British Patent Specification No. 1,464,198 teaches regeneration of phosphorus complexes with certain phosphates. These references do not disclose using vanadium-phosphorus catalysts in the presence of about 1 to about 10,000 parts per million of a peroxide to achieve improved catalyst performance and improved oxidation of the hydrocarbon feed to maleic anhydride.

This invention comprises a process for oxidizing benzene or $C_4$ hydrocarbons such as butane, butene, butadiene, and mixtures thereof to maleic anhydride by contacting it in the presence of oxygen with a vanadium-phosphorus or vanadium-phosphorus cometal catalyst in the presence of about 1 to about 10,000 parts per million by weight of a peroxide based on the total weight of the feed gas stream and for improving the performance of the vanadium-phosphorus catalyst.

In order to maintain the performance of the vanadium-phosphorus or vanadium-phosphorus cometal catalyst an alkyl ester of ortho phosphorus acid, i.e., an alkyl phosphate, is generally added in the amount of about 0.1 to about 100,000 parts per million by weight of the reactor feed gas stream. In a preferred process using continuous catalyst regeneration, the amount of alkyl phosphate added is in the range of about 0.1 to about 30 parts per million by weight of the reactor feed stream. Higher concentrations of alkyl phosphate generally above about 30 parts per million by weight are useful in a batch catalyst regeneration process, preferably in a range of about 50 to about 100,000 parts per million by weight of reactor feed gas stream and more preferably about 1000 to about 100,000 parts per million by weight of reactor feed gas stream. The reactivation is conducted at a temperature of about 650° to about 900° F. The alkyl phosphate in a water medium comprising about 0.001 to about 90 weight percent, more preferably about 0.01 to about 50 weight percent, of the solution is contacted with the feed gas stream flowing to the reactor. If desired, the water and alkyl phosphate may be added separately to the feed gas stream instead of as a solution. Alternatively, the alkyl phosphate and water may be added directly to the butane feed prior to the mixing of the butane and air reactants. The total amount of water added to the reactor feed gas stream is up to 40,000 parts per million by weight and preferably in the range of about 1000 to about 40,000 parts per million by weight.

The type of catalyst useful for this process comprises a phosphorus-vanadium mixed oxide or a phosphorus-vanadium mixed oxide promoted by metals such as molybdemun, zinc, tungsten, uranium, tin, bismuth, titanium, niobium or cobalt. The atomic ratio of the vanadium to phosphorus can suitably be in the range of 0.5:1 to 1.25:1.0. The total atomic ratio of vanadium to phosphorus advantageously is in the range of 0.75:1 to 1:1. It is preferred that the total atomic ratio of molybdenum, zinc, tungsten, uranium, tin, bismuth, titanium, niobium or cobalt to vanadium should be in the range of 0.001:1 to 0.2:1.

The cometal, such as molybdenum, zinc, tungsten, uranium, bismuth, titanium, antimony, niobium, cobalt or tin may be added as a compound together with vanadium, or seprately introduced during the preparation of the catalyst. Suitable cometal compounds comprise their oxides and soluble salts. Suitable molybdenum compounds comprise molybdenum oxide and most soluble molybdenum salts. If it is desired to improve physical properties of the catalysts, they may be treated with an inert support, for example, alumina, titania, silicon carbide, kieselguhr, pumice or silica. The catalyst may be reinforced with such materials at any stage in its preparation.

The oxidation of butane to maleic anhydride may be accomplished by contacting n-butane in low concentration in oxygen with the described catalyst. Air is entirely satisfactory as a source of oxygen, but synthetic mixtures of oxygen and diluent gases such as nitrogen may also be employed. Air enriched with oxygen may be used.

The gaseous feed stream to the oxidation reactors will normally contain air and about 0.2 to about 2.5 mole percent of the hydrocarbon such as benzene, butane, butene or butadiene. About 0.8 to about 1.8 mole percent of the hydrocarbon is satisfactory for optimum yield of maleic anhydride for the process of this invention. Although higher concentrations may be employed, explosive hazards may be encountered. Lower concentrations of the hydrocarbon feedstock, less than about one percent, of course, will reduce the productivity obtained at equivalent flow rates and, thus, are not normally employed for economic reasons. The flow rate of the gaseous stream through the reactor may be varied within rather wide limits, but the preferred range of operations is at the rate of about 100 to about 4000 cc of feed per cc of reactor volume per hour and more preferably about 1000 to about 2400 cc of feed per cc of reactor volume per hour. Lower flow rates make the butane oxidation process uneconomical. A catalyst should be effective at flow rates of about 1200 to about 2400 cc of hydrocarbon feed per cc of reactor volume per hour. There are catalysts which show good promise but when subjected to the hourly space velocity designated above show very poor yields. Residence times of the total gas stream will normally be less than about four seconds, more preferably less than about one second. The flow rates and residence times are calculated at standard conditions of 760 mm of mercury and at 0° C.

A variety of reactors will be found to be quite satisfactory including multiple tube heat exchanger-type reactors. The tops of such reactors may vary in diameter from about one-quarter inch to about three inches, and the length may be varied from about three to about sixteen or more feet. The oxidation reaction is an exothermic reaction and, therefore, relatively close control of the reaction temperatures should be maintained. It is desirable to have the reactors at a relatively constant temperature and some medium is needed to conduct heat from the reactors, such as lead and the like, but it has been found that eutectic salt baths are completely satisfactory. One such salt bath is a sodium nitrate, sodium nitrite, and potassium nitrate eutectic constant temperature mixture. An additional method of temperature control is to use a metal block reactor whereby the metals surrounding the tube act as a temperature regulating body. As will be recognized by one skilled in the art, the heat exchanger medium may be kept at the proper temperature by heat exchangers and the like. The reactor or reaction tubes may be iron, stainless steel, carbon steel, nickel, glass tubes such as vycor, and the like. Both carbon steel and nickel tubes have excellent long life under the conditions of the reaction described herein. Normally, the reactors contain a preheat zone containing an inert material such as one-quarter-inch Alundum pellets, inert ceramic balls, nickel balls, or chips and the like present at about one-half to one-tenth the volume of the active catalyst present.

The reactors that are suitable for the process of this invention may be fixed bed reactors wherein the catalyst remains stationary within the reactor, they may be fluidized bed reactors wherein the catalyst particles are continually moving within the reactor, and they may be transport or so-called moving bed reactors. In the transport bed rectors, the catalyst is moved, preferably continuously, from within the reaction zone to a second zone where the catalyst is activated. The activated catalyst is then moved back into the reaction zone for reaction with the hydrocarbon feed. By utilizing a transport bed reactor, the need for incorporating oxygen or air in the reactor feed gas stream is greatly reduced or eliminated. In this embodiment of the process, the catalyst is exposed to oxygen away from the reactor zone and it is the oxygenated catalyst that effects the oxidation reaction for converting the benzene or $C_4$ hydrocarbon to maleic anhydride.

The temperature of reaction may be varied within some limits, but normally the reaction should be conducted at a temperature within a rather critical range. The oxidation reaction is exothermic and once reaction is underway, the main purpose of the salt bath or other medium is to conduct heat away from the walls of the reactor and control the reaction. Better operations are normally obtained when the reaction temperature employed is no greater than about 20° to about 50° F. above the salt bath temperature. The temperature of the reactor, of course, will also depend to some extent upon the size of the reactor and hydrocarbon feedstock concentration.

The reaction may be conducted at atmospheric, superatmospheric or below atmospheric pressure. The exit pressure will be at least slightly higher than the ambient pressure to ensure a positive flow from the reactor. The pressure of the inert gases must be sufficiently higher to overcome the pressure drop through the reactor. The preferred pressure is from about 10 psig to about 100 psig.

We have now found that the addition of a peroxide to the reactor feed gas stream is highly beneficial for oxidation of benzene or a $C_4$ hydrocarbon feedstock to maleic anhydride using a phosphorus-vanadium or phosphorus-vanadium cometal catalyst. The use of the peroxide results in a lower reactor salt bath temperature for a given feed conversion. The lower salt bath temperature will result in prolonged catalyst lifetime, i.e., the time it takes before the catalyst deactivates and requires replacement.

Due to the expense of manufacturing the phosphorus-vanadium or phosphorus-vanadium cometal catalyst and the expenses associated with loading new catalyst into the maleic anhydride reactor, it is highly advantageous for the catalyst to have as long a useful lifetime as possible. Therefore, any means, such as the process of the instant invention, for prolonging the lifetime of the catalyst is highly desirable.

The amount of peroxide required is in the range of from about 1 to about 10,000 parts per million by weight based on the total reactor feed gas stream. Preferably, said peroxide is present in said reactor feedstream in an amount of from about 5 to about 1000 parts per million by weight.

While hydrogen peroxide is the most preferred peroxide due to availability, expense and ease of handling, other peroxides are also suitable. These other peroxides are the organic peroxides and generally include alkyl, alkenyl, aromatic, and alkyl-aromatic peroxides, hydroperoxides, peroxy acids, peroxy esters and diacylperoxides. Examples of useful organic peroxides are those peroxides selected from the group consisting of

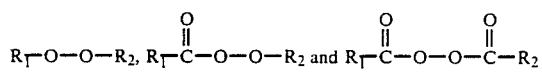

wherein $R_1$ and $R_2$ are the same or different and are selected from H or $C_1$ to $C_{10}$ alkyl, alkenyl, aromatic or alkyl aromatic hydrocarbyl substituents. The hydroperoxides are preferred over the other organic peroxides due to availability and costs. The hydroperoxides have the general formula $R_1-O-O-R_2$ where $R_2$ is H. $R_1$ is a hydrocarbon substituent as described above. Particularly preferred hydroperoxides include, for example, t-butyl hydroperoxide, amyl hydroperoxide, cyclohexyl hydroperoxide, methyl-, ethyl-, isopropyl-, n-butyl-, sec-butyl-, and tert-amyl-hydroperoxide. Mixtures of the peroxides described above are also useful.

In addition to lowering the salt bath temperature for the maleic anhydride oxidation reaction, the addition of a peroxide such as hydrogen peroxide provides other benefits. For example, hydrogen peroxide is known to decompose thermally to water and oxygen. As already mentioned, water is added to the phsophorus-vanadium cometal catalyst along with the alkyl phosphate. Therefore, when hydrogen peroxide decomposes, additional water is supplied to the catalyst. Also, the decomposition of the hydrogen peroxide supplies additional oxygen required for the oxidation reaction.

The peroxide can be added to the feed gas stream by any one of a number of methods. The method of addition used is not crucial to the invention. However, it may be added dropwise to the reactor feed gas stream or sprayed or added as a vapor to the reactor feed gas stream.

Maleic anhydride may be recovered by a number of ways well known to those skilled in the art. For example, the recovery may be by direct condensation or by absorption in suitable media.

In summary, the disclosed process comprises the vapor-phase oxidation of benzene or $C_4$ hydrocarbon feedstock in a reactor to form maleic anhydride in which benzene or the $C_4$ hydrocarbon is contacted in the presence of air or molecular oxygen or other oxygen containing gas with a catalyst comprising vanadium and phosphorus wherein at least one peroxide is added to the reactor feed gas stream in an amount of from about 1.0 part per million to about 10,000 parts per million by weight of the total reactor feed gas stream.

The following examples will serve to provide a fuller understanding of the invention, but it is to be understood that these examples are given for illustrative purposes only and should not be interpreted as limiting the invention in any way.

EXAMPLE 1

Typical Catalyst Preparation

To a 3-liter, 3-neck, round bottom flask equipped with a thermowell, electrical mantle, mechanical stirrer, and reflux condenser, were added 364 g $V_2O_5$, 17.28 g $MoO_3$, 270 g water, and 1,000 ml tetrahydrofuran (THF). $POCl_3$(767 g) was added from an addition funnel over a period of 2 hours. During the $POCl_3$ addition an exothermic reaction occurred which resulted in a continuous temperature rise, reflux of the solvent and dissolution of the solids. The mixture turned from a yellow orange slurry to red brown solution as the $POCl_3$ addition progressed. At the end of $POCl_3$ addition the deep green solution was heated up to reflux and maintained at reflux for 2 hours. The deep green solution was then partially (500 ml) stripped of solvent. The thick black, green syrup was then dried overnight at about 3 in of Hg vacuum with a mild air, nitrogen, or $N_2$/air purge passing through the oven. Drying temperature and time varied from 130° C. to 200° C. and 18 to 48 hours respectively.

The dark brown catalyst powder was ground, calcined at 300° C. in air for 4 hours and formed into 3/16 in cylindrical tablets using 5 wt. % graphite as a lubricant. The side crush strength of the tablets was about 5.9 lbs.

EXAMPLE 2

Addition of a Peroxide to a 4 Ft. Maleic Anhydride Pilot Plant Reactor

Table 1 presents the results of the oxidation of n-butane with air in a 4 ft by 0.75 in pilot plant reactor loaded with a phosphorus-vanadium cometal oxidation catalyst. For Run A, with no added hydrogen peroxide, the n-butane conversion was 75 mol % with a salt bath temperature of 751° F. The catalyst was on stream for 170 days. For Run B, 500 parts per million by weight of hydrogen peroxide were added to the reactor feed gas stream for a period of 15 days. The conversion remained at 75 mol %; however, the salt bath temperature dropped to 731° F., indicating that the same conversion can be achieved at a substantially lower salt bath temperature if a peroxide is added to the feed gas stream.

For Run C in Table 1, the hydrogen peroxide was removed from the feed gas stream. The salt bath temperature increased to 752° F.; however, for Run D hydrogen peroxide was again added at the 250 parts per million level and the salt bath temperature decreased to 720° F. Conversion of the n-butane, however, remained at 75 mol % throughout these changes.

The data clearly demonstrate that the introduction of a peroxide to the reactor feed gas stream permits using a lower salt bath temperature and, furthermore, that the effect of the added peroxide on the salt bath temperature is reversible.

TABLE 1

| | Addition of Peroxide to Reactor Feed Gas Stream - 4 Ft Reactor[a] | | | |
|---|---|---|---|---|
| | Days on | | | n-Butane |
| Run No. | Conversion[c] Stream | Concentration, ppm[b] | Feed $H_2O_2$ Temp., °F. | Salt Bath Mol % |
| A | 170 | 0 | 751 | 75 |
| B | 185 | 500 | 731 | 75 |
| C | 210 | 0 | 752 | 75 |
| D | 235 | 250 | 720 | 75 |

[a]Air rate = space velocity of 2000/hr Feed n-butane concentration = 1.5 mol % Feed moisture concentration = 10,000 parts per million Feed triethyl phosphate concentration = 5 parts per million
[b]parts per million
[c]Conversion = $\frac{\text{moles n-butane reacted}}{\text{moles n-butane in feed}} \times 100$

EXAMPLE 3

Addition of a Peroxide to a 16 Ft. Maleic Anhydride Pilot Plant Reactor

Table II shows the results for the oxidation of n-butane with air in a 16 ft by 1 in. pilot plant reactor loaded with a phosphorus-vanadium cometal catalyst. In Run E, no hydrogen peroxide was added to the reactor feed gas stream. The salt bath temperature was 759° F. and the n-butane conversion was 87.5%. The catalyst was on stream for 44 days. In Run F, 30 parts per million of hydrogen peroxide were added to the feed gas stream. The temperature of the bath decreased to 745° F. while the n-butane conversion remained at 87.5 mol %. Thus, in the larger 16 ft reactor the same effect was observed as in the 4 ft reactor. Even at the 30 parts per million level, the added peroxide substantially reduced the reactor salt bath temperature required to achieve a conversion equivalent to that obtained without the use of the hydrogen peroxide.

TABLE II

| | Addition of Peroxide to Reactor Feed Gas Stream - 16 Ft Reactor[a] | | | |
|---|---|---|---|---|
| Run No. | Days on Stream | Feed $H_2O_2$ Concentration ppm[a] | Salt Bath Temp., °F. | n-Butane Conversion Mole %[a] |
| E | 44 | 0 | 759 | 87.5 |
| F | 61 | 30 | 745 | 87.5 |

[a]See footnotes in Table I

We claim:
1. A process comprising the vapor-pahse oxidation of benzene or $C_4$ hydrocarbon feedstock in a reactor to form maleic anhydride in which benzene or the $C_4$ hydrocarbon is contacted in the presence of air or molecular oxygen or other oxygen containing gas with a catalyst comprising vanadium and phosphorus wherein at least one peroxide is added to the reactor feed gas stream in an amount of from about 1.0 part per million to about 10,000 parts per million by weight of the total reactor feed gas stream.

2. The process of claim 1 wherein the reactor is a fixed bed reactor.

3. The process of claim 1 wherein the reactor is a fluidized bed reactor.

4. The process of claim 1 wherein the reactor is a transport bed reactor.

5. The process of claim 1 wherein said peroxide is hydrogen peroxide.

6. The process of claim 1 wherein said peroxide is selected from the group consisting of

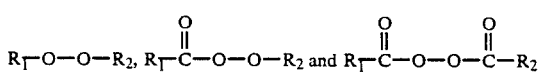

wherein $R_1$ and $R_2$ are the same or different, and are H or a hydrocarbyl group having from 1 to 10 carbon atoms, said hydrocarbyl group being alkyl, alkenyl, aromatic or alkyl aromatic.

7. The process of claim 1 wherein said peroxide is a hydroperoxide having structure $R_1$—O—O—H wherein $R_1$ is a hydrocarbyl group having from 1 to 10 carbon atoms and wherein said hydrocarbyl group is alkyl, alkenyl, aromatic or alkyl aromatic.

8. A process for the vapor-phase oxidation of benzene or $C_4$ hydrocarbon feedstock to form maleic anhydride in which benzene or the $C_4$ hydrocarbon is contacted in the presence of molecular oxygen or air at an hourly space velocity of about 100 to 4000 cubic centimeters of feed per cubic centimeter of catalyst per hour with a vanadium-phosphorus cometal catalyst wherein the cometal is selected from the group consisting of zinc, molybdenum, niobium, tungsten, uranium, cobalt and tin wherein the catalyst is regenerated continuously or batchwise by contacting it during the vapor-phase oxidation with an alkyl ester of orthophosphoric acid having the formula $(RO)_3P=O$ where R is hydrogen or a $C_1$ to $C_4$ alkyl, at least one R being a $C_1$ to $C_4$ alkyl, the alkyl ester being added in an amount of from about 0.1 to about 100,000 parts per million by weight of the reactor feed gas stream, and wherein water and at least one peroxide are added to the feed gas stream, said water being added in an amount of up to about 40,000 parts per million by weight of the total reactor feed gas stream and said peroxide being added in an amount of from about 1.0 to about 10,000 parts per million by weight of the total reactor feed gas stream.

9. The process of claim 8 wherein said peroxide is selected from the group consisting of

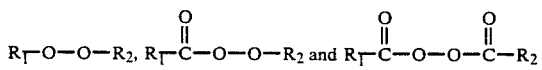

wherein $R_1$ and $R_2$ are the same or different, and are H or a hydrocarbyl group having from 1 to 10 carbon atoms, said hydrocarbyl group being alkyl, alkenyl, aromatic or alkyl aromatic.

10. The process of claim 8 wherein said peroxide is a hydroperoxide having structure $R_1$—O—O—H wherein $R_1$ is a hydrocarbyl group having from 1 to 10 carbon atoms and wherein said hydrocarbyl group is alkyl, alkenyl, aromatic or alkyl aromatic.

11. The process of claim 8 wherein the alkyl ester is triethylphosphate.

12. The process of claim 8 wherein the alkyl ester is trimethylphosphate.

13. The process of claim 8 wherein the reaction temperature is about 650° F. to about 900° F.

14. The process of claim 8 wherein the reaction pressure is from about 10 psig to about 100 psig.

15. The process of claim 8 wherein a fixed-bed catalyst is used and the feedstock contains about 0.2 to about 3.5 mol percent butane, and the hourly space velocity is in the range of about 1000 to about 2400 cubic centimeters of feed per cubic centimeter of catalyst per hour.

16. The process of claim 8 wherein said peroxide is hydrogen peroxide.

17. The process of claim 16 wherein the hydrogen peroxide is added to the total reactor feed in an amount of from about 5 to about 1000 parts per million by weight of the total reactor feed gas stream.

18. A continuous process for the vapor-phase oxidation of benzene or $C_4$ hydrocarbon feedstock to form maleic anhydride in which benzene or the $C_4$ hydrocarbon is contacted in the presence of molecular oxygen or air at an hourly space velocity of about 100 to 4000 cubic centimeters of feed per cubic centimeter of reactor volume per hour with a vanadium-phosphorus cometal catalyst wherein the cometal is selected from the group consisting of zinc, molybdenum, niobium, tungsten, uranium, cobalt and tin wherein the catalyst is regenerated continuously by contacting it during the vapor-phase oxidation with an alkyl ester of orthophosphoric acid having the formula $(RO)_3P=O$ where R is hydrogen or a $C_1$ to $C_4$ alkyl, at least one R being a $C_1$ to $C_4$ alkyl, the alkyl ester being added in an amount of from about 0.1 to about 30 parts per million by weight of the total reactor feed gas stream, and wherein water and hydrogen peroxide are added to said reactor feed gas stream, said water being added in an amount up to about 40,000 parts per million by weight of the total reactor feed gas stream and said hydrogen peroxide being added in an amount of from about 1 to about 10,000 parts per million by weight of the total reactor feed gas stream.

19. The process of claim 18 wherein the alkyl ester is triethylphosphate.

20. The process of claim 18 wherein the alkyl ester is trimethylphosphate.

21. The process of claim 18 wherein the reaction temperature is about 650° F. to about 900° F.

22. The process of claim 18 wherein the reaction pressure is from about 10 psig to about 100 psig.

23. The process of claim 18 wherein a fixed-bed catalyst is used and the feedstock contains about 0.2 to about 2.5 mol percent butane and the hourly space velocity is in the range of about 1000 to about 2400 cubic centimeters of feed per cubic centimeter of catalyst per hour.

24. The process of claim 18 wherein the amount of hydrogen peroxide added is about 5 parts per million to about 1000 parts per million by weight of the total reactor feed gas stream.

25. A continuous process for the vapor-phase oxidation of butane feedstock to form maleic anhydride in which butane is contacted in the presence of molecular oxygen or air at an hourly space velocity about 100 to 4000 cubic centimeters of feed per cubic centimeter of reactor volume per hour with a vanadium-phosphorus catalyst promoted by zinc or molybdenum wherein the catalyst is regenerated continuously or batchwise by contacting it during the vapor-phase oxidation with an alkyl ester of orthophosphoric acid having the formula $(RO)_3P=O$ where R is hydrogen or a $C_1$ to $C_4$ alkyl, at least one R being a $C_1$ to $C_4$ alkyl, wherein the alkyl ester is added in an amount of from about 0.1 to about 100,000 parts per million by weight of the total reactor feed gas stream, and wherein water and hydrogen peroxide are added to said reactor feed gas stream, said water being added in an amount up to about 40,000 parts per million by weight of the total reactor feed gas stream and said hydrogen peroxide being added in an amount of from about 1 to about 10,000 parts per million of the total reactor feed gas stream.

26. The process of claim 25 wherein the alkyl ester is triethylphosphate.

27. The process of claim 25 wherein the alkyl ester is trimethylphosphate.

28. The process of claim 25 wherein the reaction temperature is about 650° F. to about 900° F.

29. The process of claim 25 wherein the reactor pressure is from about 10 psig to about 100 psig.

30. The process of claim 25 wherein a fixed-bed catalyst is used and the feedstock contains about 0.2 to about 2.5 mol percent butane and the hourly space velocity is in the range of about 1000 to about 2400 cubic centimeters of feed per cubic centimeter of catalyst per hour.

31. The process of claim 25 wherein the amount of hydrogen peroxide added is about 5 parts per million to about 1000 parts per million by weight of the total reactor feed gas stream.

* * * * *

UNITED STATES PATENT OFFICE
CERTIFICATE OF CORRECTION

Patent No. 4,950,769         Dated August 21, 1990

Inventor(s) Henry A. McCandless, John L. Cearley and Hassan Taheri

It is certified that error appears in the above-identified patent and that said Letters Patent is hereby corrected as shown below:

| Col. | Line |  |
|---|---|---|
| 9 | 16-17 | "per million of the" should read --per million by weight of the-- |

Signed and Sealed this

Twenty-fifth Day of February, 1992

Attest:

HARRY F. MANBECK, JR.

Attesting Officer    Commissioner of Patents and Trademarks